United States Patent [19]

Cannon

[11] Patent Number: 5,266,330
[45] Date of Patent: Nov. 30, 1993

[54] METHOD FOR TREATING PRESSURE ULCERS USING CALENDULA

[76] Inventor: Karen A. Cannon, 14 Randall St., North Easton, Mass. 02356

[21] Appl. No.: 900,117

[22] Filed: Jun. 18, 1992

[51] Int. Cl.$^5$ ............................................... A61L 15/00
[52] U.S. Cl. ................................ 424/445; 424/443; 424/446; 424/447; 424/195.1; 514/928
[58] Field of Search ............... 424/445, 443, 446, 447, 424/195.1; 514/928

[56] References Cited

U.S. PATENT DOCUMENTS

| | | | |
|---|---|---|---|
| 116,906 | 7/1871 | Williams | 424/447 |
| 327,933 | 7/1885 | Eyermann | 424/195.1 |
| 395,824 | 1/1889 | Gentry | 424/195.1 |
| 4,719,111 | 1/1988 | Wilson | 514/925 |

FOREIGN PATENT DOCUMENTS 3407024  9/1985  Fed. Rep. of Germany .

OTHER PUBLICATIONS

E. F. Steinmetz, Codex Vegetalis, 1957.
The New Age Herbalist, Richard Mabey, ed., 1988, p. 46.

*Primary Examiner*—Thurman K. Page
*Assistant Examiner*—D. Gabrielle Phelan
*Attorney, Agent, or Firm*—David H. Judson; Mary E. Raynor

[57] ABSTRACT

A method for treating human pressure ulcer conditions of bedridden patients using an effective amount of the plant extract *calendula officinalis L.* in a topical pharmaceutical carrier selected from the group consisting of ointments, lotions, pastes, solvents, jellies, sprays and aerosols. The calendula is present by weight from about 1.0 to 25.0%. Preferably, pressure ulcers are treated by soaking sterile dressings in a 2.5% solution of calendula in saline, and then applying such dressings to the affected area.

9 Claims, No Drawings

METHOD FOR TREATING PRESSURE ULCERS USING CALENDULA

TECHNICAL FIELD

The present invention relates generally to methods for treating human disease conditions and more particularly to use of the plant extract calendula to treat ulcerative skin conditions.

BACKGROUND OF THE INVENTION

Patients bedridden in hospitals or other long-term care facilities often exhibit ancillary health problems due to the nature of the care itself. Such patients are typically incontinent and remain prone and in bed for extended periods of time, and as a result often develop pressure ulcers or other similar maladies which require medical intervention. Often these secondary problems are more discomforting than the primary ailment being treated.

It is known in the prior art to treat such pressure ulcers with a wide variety of medicaments. Commercial products include Granulex, Silvadene and Domeboro soak solutions. Typically, the patient is treated with the soak solution several times per day depending on the patient's physical condition and nutritional status. These prior art substances and techniques, however, do not provide satisfactory results.

There remains a need to provide improved techniques and methods for treating pressure ulcers that overcome these and other problems associated with the prior art.

BRIEF SUMMARY OF THE INVENTION

It is the principal object of the present invention to describe a method for treating human pressure ulcer conditions using the plant extract calendula. The extract is applied to the skin in a topically-acceptable carrier or other suitable excipient in the form of an ointment, paste, lotion, cream, solution, jelly, aerosol, spray or the like. When the solution preparation is used, it is preferable to soak the solution into suitable gauze or other sterile dressings that are then applied to the ulcer.

It is a further object of the invention to describe a method for treating human pressure ulcer conditions of bedridden patients using an effective amount of the plant extract *calendula officinalis L.* in a topical pharmaceutical carrier selected from the group consisting of ointments, lotions, pastes, solvents, jellies, sprays and aerosols. The calendula is present by weight from about 1.0 to 25.0%, and preferably 2.5%, of the pharmaceutical preparation. For example, one particularly effective preparation comprises 2.5% calendula oil in a saline base.

It is a further object of the invention to describe a method for preventing human pressure ulcer conditions of a bedridden patient comprising the step of applying calendula, in a topically acceptable carrier or excipient, to the skin of the bedridden patient in one or more areas of the skin susceptible to ulceration. In this embodiment, it has been found that a petrolatum base is a preferable carrier material The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

DETAILED DESCRIPTION

In a first embodiment of the invention, calendula is used to treat decubitis or diabetic ("pressure") ulcers. In a second embodiment, calendula is used as a preventative to prevent the formation of such ulcers.

*Calendula officinalis L.* is a known substance derived from the marigold plant. The calendula plant extract is available commercially in the form of an oil or particulate. It has been used in the past for treating sunburn, superficial wounds and dry skin, among other human disease conditions. According to the present invention, a method for treating human pressure ulcerative conditions in a bedridden patient is achieved by applying an effective amount of the plant extract *calendula officinalis L.* in a topical pharmaceutical carrier to the pressure ulcer. Although not meant to be limiting, preferably the composition is applied directly or indirectly (e.g., through a soaked sterile dressing or the like) three-four times a day or until granulation of the ulcer occurs (indicating healing has begun) The precise duration of the treatment will typically vary according to each individual taking into consideration physical condition and nutritional status prior to treatment.

The calendula-based pharmaceutical compositions contemplated by this invention include pharmaceutical compositions for topical and local action. The term "topical" as employed herein relates to the use of any calendula compound incorporated in a suitable pharmaceutical carrier, and applied at the site of the pressure ulcer for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, solvents, sprays, aerosols and the like. The term "ointment" embraces formulations (including creams) having oleaginous, absorption, water-soluble and emulsion-type bases, e.g., petrolatum, lanolin, polyethylene glycol, as well as mixtures of these.

The percentage by weight of the calendula compound herein utilized ranges from about 1.0% to about 25% of the pharmaceutical preparation. The preferred percentage is 2.5%. In these preparations the aforesaid pharmaceutical carrier for topical application constitutes the major amount of said preparation.

The following examples describe the manner and process of making and using the invention and set forth the preferred mode contemplated by the inventor of carrying out the invention but are not to be construed as limiting.

A calendula preparation was formed by mixing 10cc of calendula tincture in 1000 cc normal saline. The resulting solution was used to soak several sterile 4"×4" cotton gauze or similar sterile dressings. The dressings were then applied to a clean open area of the ulcer, and a plastic barrier was used to cover the gauze. The preparation was then allowed to soak on the wound for at least 20 minutes. After this time, the barrier and dressings were removed and the treated area allowed to dry. No dressing was applied or considered necessary. This procedure was repeated three-four times a day until the ulcer cleared. After the first few days of treatment, the percentage by weight of calendula may be gradually decreased as the ulcer begins to heal.

A second calendula preparation was formed by mixing 20 cc calendula tincture 20 cc in 1000 cc normal saline. Using this preparation, the above-identified technique was repeated. The slightly higher concentration decreased healing time. Once the pressure ulcer reaches a stage 1 classification (indicating the initial onset of the ulceration), the patient is preferably treated with a maintenance preparation comprising a mixture of about 2.5% by weight of calendula in petrolatum. Usually patients with decubitis ulcers continue to have skin breakdown after healing takes place, however, it has been found that by increasing the concentration to about 2% the healing time for repeat open areas decreased.

Based on experimental testing, it has been found that depending on the patient's physical, nutritional and mobile state, the average healing time from a stage 2 to stage 1 condition was between two to three weeks. The following describe several experimental tests of the inventive treatment method.

In a first case, a ninety year old female presented with chronic open areas (pressure ulcers) on her buttocks and midback. Areas always were open (stage 2) and no positive results were seen with Granulex spray. According to the invention, a 2% calendula-in-saline soak was begun three times per day and healing was obtained on all areas within two to three weeks.

In a second case, a seventy year old female with multiple physical problems (CVA with aphasia, G-tube, contractures and incontinence) was being treated with a Domeboro soak solution for a stage 3 pressure ulcer measuring approximately 4-5 cm on her coccyx area. The Domeboro solution had been in usage for three or four weeks and no improvement was noticed. The area was extremely sensitive. After unsuccessful attempts to relieve the problems using Granulex spray and Silvadene ointment, the present invention was used. Calendula was diluted with normal saline and a saturated dressing was applied to the open area for one hour. Later on that evening, the soak was reapplied for an additional hour. The patient was then repositioned on her side allowing the air to flow freely around the ulcer. Following this treatment methodology, the area healed within ten days even though only two soaks were applied each day. After the fourth treatment the area was no longer sensitive to pressure.

In a third case, an eighty six year old male presented with numerous diabetic ulcers of his only leg. His ankle area had a stage 3 (possible stage 4) ulcer of about 5-6 cm, and his shin area had a stage 2 lesion with necrotic tissue. Domepaste boot was the treatment of choice and no improvement was seen after 6-8 weeks. Thereafter, according to the invention calendula soaks were applied 4 times per day for 20 minutes. Within seven days the necrotic tissue was gone and both areas began to granulate. By the fourth week the ulcer on the patient's ankle was stage 2 and the area on his shin almost healed. After drainage problems (unrelated to the treatment), the patient was sent to the emergency room and was treated with a Domepaste boot. Ten days after the boot treatment was in place, the boot was removed. The shin ulcer was found to be a stage 3 with the tendon exposed and the ankle area at least a stage 3. Thus cessation of the treatment (and use of prior art techniques) had caused deterioration of the patient's condition.

The present invention solves these problems of the prior art. Although not meant to be limiting, preferably the treatment involves use of calendula soaks on stage 2 open areas. The open areas may be located anywhere on the patient's body. When Calendula soaks were used faithfully three or four times per day, granulation always takes place. The duration of the treatments vary according to each individual resident, taking into consideration physical condition and nutritional status. Stage 1 pressure areas are treated with Calendula and Vaseline for prevention.

It should be appreciated by those skilled in the art that the specific embodiments disclosed above may be readily utilized as a basis for modifying or designing other techniques for carrying out the same purposes of the present invention. It should also be realized by those skilled in the art that such equivalent methods do not depart from the spirit and scope of the invention as set forth in the appended claims.

I claim:

1. A method for treating a human ulcerative skin condition by applying to an ulcer a preparation containing about 1 to 25% by weight calendula in a topically-acceptable carrier comprising a saline solution until healing is obtained.

2. The method as described in claim 1 wherein the step of applying the calendula includes the step of soaking a sterile dressing with the solution and applying the soaked dressing to the ulcer.

3. The method as described in claim 2 wherein the step of applying the soaked dressing to the ulcer is repeated at least twice a day.

4. The method as described in claim 3 further including the step of removing the soaked dressing from the ulcer and allowing the ulcer to dry out.

5. The method as described in claim 3 further including the step of decreasing the percentage of calendula in the solution as the ulcer begins to heal.

6. The method as described in claim 3 further including the step of applying a calendula preparation after the ulcer has healed to prevent reoccurrence of the condition.

7. A method for treating a human ulcerative skin condition comprising the steps of:
 mixing about 1-25% by weight calendula in a saline solution to form a topically-acceptable preparation;
 soaking a sterile dressing in the preparation to form a soak;
 applying the soak to the ulcer at least once per day until granulation of the ulcer begins; and
 applying a maintenance dressing of calendula after such granulation begins.

8. The method as described in claim 7 further including the step of removing the soak from the ulcer and allowing the ulcer to dry out prior to reapplication.

9. The method as described in claim 7 further including the step of decreasing the percentage of calendula in the topically-acceptable preparation as the ulcer begins to heal.

* * * * *